United States Patent [19]
Haginaka et al.

[11] Patent Number: 6,027,648
[45] Date of Patent: Feb. 22, 2000

[54] METHOD OF RESOLVING A MIXTURE OF OPTICAL ISOMERS

[75] Inventors: Jun Haginaka, Kalamazoo, Mich.; Hiroo Wada; Hiroya Fujima, both of Kyoto, Japan; Toshinobu Miwa, Aichi, Japan

[73] Assignees: Shinwa Chemical Industries, Ltd., Kyoto; Eisai Co., Ltd., Tokyo, both of Japan

[21] Appl. No.: 08/201,740

[22] Filed: Feb. 25, 1994

Related U.S. Application Data

[62] Division of application No. 07/795,862, Nov. 18, 1991, abandoned.

[30] Foreign Application Priority Data

Nov. 21, 1990 [JP] Japan ................................. 2-320058

[51] Int. Cl.⁷ .......................... B01D 15/00; B01D 15/08; C07B 57/00
[52] U.S. Cl. .................. 210/635; 210/198.2; 210/502.1; 210/656
[58] Field of Search .................................. 210/638, 635, 210/656, 198.2, 502.1

[56] References Cited

U.S. PATENT DOCUMENTS

| | | | |
|---|---|---|---|
| 4,830,921 | 5/1989 | Kitayama et al. | 210/656 X |
| 5,030,354 | 7/1991 | Miwa et al. | 210/656 X |
| 5,063,081 | 11/1991 | Cozzete et al. | 204/153.12 X |

*Primary Examiner*—John Kim
*Attorney, Agent, or Firm*—Flynn, Thiel, Boutell & Tanis, P.C.

[57] ABSTRACT

An optical isomer separating agent comprises a stationary phase in which the molecular structure of ovomucoid fixed to a carrier is partly modified, or a stationary phase in which ovomucoid having the molecule partly modified is fixed to a carrier is disclosed. A process for producing an optical isomer separating agent comprises the steps of immobilizing ovomucoid on a carrier and modifying the ovomucoid is disclosed. Furthermore a process for producing an optical isomer separating agent comprises the steps of modifying ovomucoid and immobilizing the modified ovomucoid on a carrier is disclosed.

7 Claims, 1 Drawing Sheet

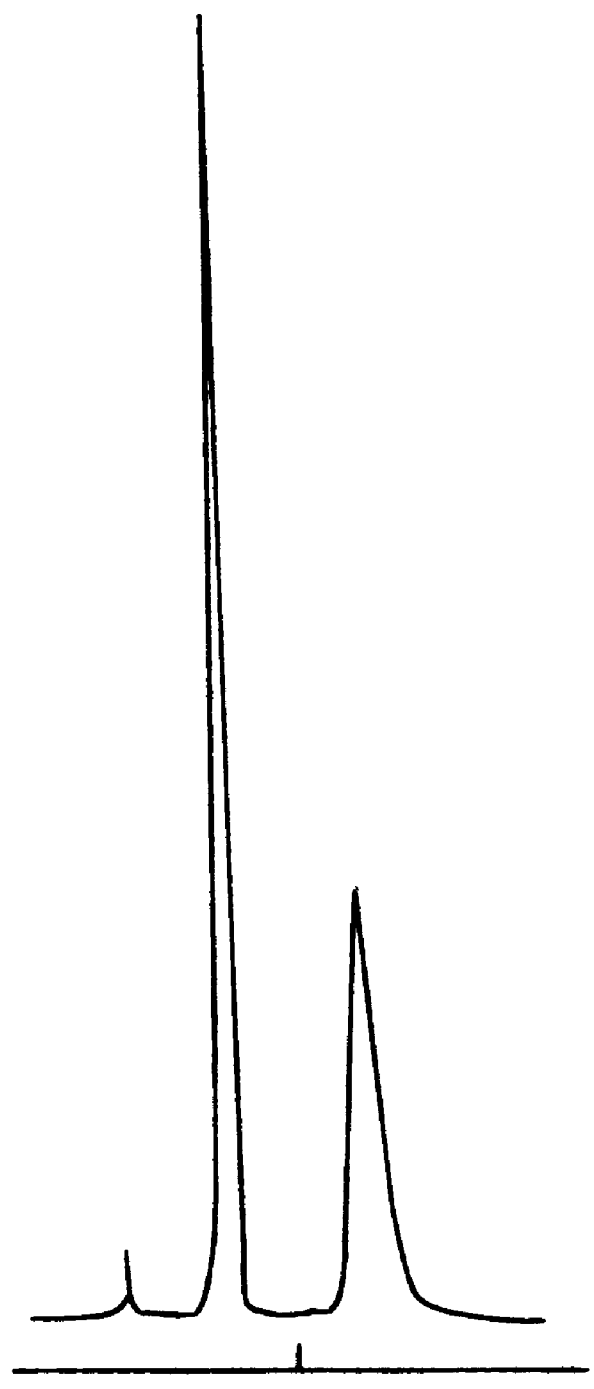

METHOD OF RESOLVING A MIXTURE OF OPTICAL ISOMERS

This is a division of Ser. No. 07/795,862, filed Nov. 18, 1991, abandoned.

BACKGROUND OF THE INVENTION

1. Field of the Invention

This invention relates to optical isomer separating agents using ovomucoid the molecular structure of which is partly modified.

2. Description of Related Arts

For chiral chemical substances containing asymmetric carbon atoms, the separation of their optical isomers is strongly desired, particularly, in the field of pharmaceuticals. Namely, it has been established as a general fact that one of a plurality of optical isomers constituting one racemic body shows particularly remarkable pharmaceutical utilities, for example, remarkable pharmacological effect and remarkable availability in vivo, or conversely, remarkable toxicity, and thus, as pharmaceuticals, administration in the form of a separated optical isomer is more rational than that in the form of a racemic body, resulting in an enhancement in remedial effect.

Various laboratory methods for separation of optical isomers have been reported so far, but those practicable in industrial scale are few, which has been considered to be an extremely difficult technical problem. However, in accordance with the progress of column chromatography, particularly, the separation of optical isomers by liquid chromatography comes to be known, as shown in following references (1)–(3).

(1) D. W. Armstrong et al., Journal of Chromatographic Science, Vol. 22 (1984), 411–415.
(2) Jörgen Hermansson, Journal of Chromatography, 325 (1985), 379–384.
(3) I. W. Wainer et al., Journal of Chromatography, 284 (1984), 117–124.
(4) S. Allenmark et al., Journal of Chromatography, 264 (1983), 63–68.
(5) S. Allenmark et al., Journal of Chromatography, 237 (1982), 473–477.
(6) U. S. Pat. No. 4,539,399
(7) Japanese Patent Application OPI No. 60-41619
(8) T. Miwa et al., Chemical and Pharmaceutical Bulletin, Vol. 35 (1987), 682–686.

Among the references described above, (1) discloses the separation using cyclodextrin, and (6) discloses the separation using a stationary phase having cyclodextrin bonded to silica gel. (2) discloses a technique using 1-acidic glycoprotein, and (3) discloses a technique using (R)-N-(3,5-dinitrobenzoyl)phenylglycine. (4) and (5) disclose the separation using stationary phases having bovine serum albumin bonded to silica and agarose, respectively. (7) discloses the separation using orosomucoid and its functional analogs, and (8) discloses the separation using a stationary phase having ovomucoid bonded to a carrier.

However, the materials used in the techniques of (1)–(7) are generally expensive. Further, as these techniques mainly adopts liquid chromatographic separation requiring large quantities of organic solvents, the used materials must be stable to the deformation of the organic solvents. However, albumin and ovomucoid, for example, can not sufficiently satisfy this condition.

In the method of (8), a comparatively inexpensive material, ovomucoid, is used in the form of an optical isomer separating agent by bonding it to silica gel, cellulose, or synthetic polymers, but this method has a disadvantage in that much time is required for re-equilibration at the time of eluate exchange, and also,, optical resolution is often insufficient. For example, propranolol and alprenolol which are β-blockers does not provide sufficient optical resolution.

SUMMARY OF THE INVENTION

In view of the problems described above, the present inventors paid attention to ovomucoid, and as a result of the earnest studies on enhancement in its optical resolving force for a long time, we have found that the purpose can be achieved by synthesizing a stationary phase in which the molecular structure of ovomucoid fixed to a carrier is partly modified or a stationary phase in which ovomucoid having the molecule partly modified is bonded, and attained this invention.

Namely, this invention provides an optical isomer separating agent comprising a stationary phase in which the molecular structure of ovomucoid fixed to a carrier is partly modified, or a stationary phase in which ovomucoid having the molecule partly modified is fixed to a carrier.

The invention provides a separating agent for optical isomers comprising ovomucoid part of which has been modified and a carrier on which the modified ovomucoid has been immobilized.

The invention further provides a process for producing the separating agent comprising the steps of immobilizing ovomucoid on a carrier and modifying the ovomucoid. Another process is provided, comprising the steps of modifying ovomucoid and immobilizing the modified ovomucoid on a carrier.

DETAILED DESCRIPTION OF THE INVENTION

This invention is further illustrated in detail.

Ovomucoid is a glycoprotein having an isoelectric point of 3.9–4.5 present in albumen. It is easy to separate from other general proteins because it is not thermally coagulable nor precipitable with trichloroacetic acid. It can be obtained, for example, by treating albumen at 75–100° C. to thermally coagulate most of proteins other than ovomucoid and adding ethanol to the resulting supernatant followed by precipitation and collection, or by adding an equal quantity of 0.5 M trichloroacetic acid-acetone mixture (1:2 by volume) to albumen having pH adjusted to 3.5 to precipitate other proteins, and adding 2- to 3-fold volume of acetone to the resulting supernatant followed by precipitation and collection. It is also easily fractionated as by-products from the residual solution after lysozyme or conalbumin is collected from albumen. In this invention, the ovomucoids thus produced at a low price may be sufficiently used, and no particular limitation is required.

The chemical modification of the molecules of proteins is generally performed by chemical, enzymic, and physical methods. Namely, when attention is given to the amino, imidazole, and carboxyl groups in the protein molecule, and aldehydes, acid anhydrides, and alcohols are reacted with them, Schiff's bases, N-substituted imidazole groups, and esters are produced to achieve the chemical modification, and further, when various effects possessed by enzymes are utilized, reactions such as modification of functional groups, oxidation and reduction of molecules, and partial removal of molecules can be performed under moderate conditions.

For example, a partly glutarized ovomucoid can be obtained as follows.

Ovomucoid and glutaraldehyde are added to phosphate buffer solution of pH 6.8 followed by stirring at 30° C. for 15 hours to form a glutarized ovomucoid (non-reduced type), or, further using sodium borohydride, stirring is carried out in phosphate buffer solution of pH 6.8 at 4° C. for 12 hours for reduction, and the formed glutarized ovomucoid (reduced type) is purified.

The purification of the glutarized ovomucoid can be performed by methods generally used without any particular limitation. For example, the unreacted glutaraldehyde and sodium borohydride can be removed from the above reaction solution by use of Sephadex G25 column chromatography.

A partly diolated ovomucoid can be obtained by adding ovomucoid and 2,3-epoxypropanol to phosphate buffer solution of pH 8.0 followed by stirring at room temperature for 24 hours, and purifying the formed diolated ovomucoid.

A partly acylated ovomucoid can be obtained by adding ovomucoid and a corresponding acid anhydride to borate buffer solution of pH 8.5 followed by stirring at 25° C. for 30–60 minutes, and purifying the formed acylated ovomucoid.

As the carriers used in this invention, any carrier which can be combined with ovomucoid having the molecule partly modified to form a stationary phase may be used. The separation of the optical isomers according to this invention is mainly performed by liquid chromatography, and examples of the carriers include silica gel, glass, cellulose, carbon, synthetic polymers, and the like.

To obtain a stationary phase in which the ovomucoid having the molecule partly modified is bonded to a carrier, ovomucoid whose molecule was partly modified is bonded to a carrier by covalent bond and ionic bond, or a stationary phase in which ovomucoid was preliminarily bonded is subjected to the modification according to the method described before to form the intended stationary phase.

The ovomucoid or ovomucoid whose molecule is partly modified (hereinafter referred to as ligand) may be bonded to the carrier according to methods generally used to form stationary phases. Thus, considerable methods are to bond the ligand by use of aminopropyl silica gel, and carbons and synthetic polymers to which amino group is bonded as the carriers and glutaraldehyde and N,N-disuccinimidyl carbonate as cross-linking agents, to bond the ligand by use of silica gel and glass as the carriers and 3-glycydoxypropyl trimethoxysilane as the cross-linking agent, to use cellulose as the carrier, activate it with cyanogen bromide, and then bond the ligand thereto, and to bond the ligand with anion exchange synthetic polymers.

The method to bond the glutarized ovomucoid to aminopropyl silica gel is specifically described below.

A glutarized ovomucoid is dissolved in sodium hydrogencarbonate buffer solution of pH 6.8. Separately, aminopropyl silica gel and N,N-disuccinimidyl carbonate are dissolved and suspended in sodium hydrogencarbonate buffer solution of pH 6.8 followed by stirring for one night, and the resulting activated aminopropyl silica gel is taken out and washed with water. Then the resulting activated aminopropyl silica gel is suspended in sodium hydrogencarbonate buffer solution of pH 6.8 to obtain a suspension of the activated aminopropyl silica gel. The glutarized ovcmucoid solution prepared beforehand is added to the activated aminopropyl silica gel suspension followed by stirring, and then washed with water to obtain an optical isomer separating agent in which the glutarized ovomucoid is bonded to silica gel through the cross-linking agent.

The ovomucoid on the stationary phase in which ovomucoid is preliminarily bonded can be chemically modified as follows.

For example, a carrier in which a polyamine such as pentaethyl hexamine is introduced into a hydrophilic synthetic polymer, and N,N-disuccinimidyl carbonate are dissolved and suspended in sodium hydrogencarbonate buffer solution of pH 6.8 followed by stirring for one night, and the resulting activated synthetic polymer is taken out and washed with water. Then the resulting activated synthetic polymer is suspended in sodium hydrogencarbonate buffer solution of pH 6.8 to obtain a suspension of the activated synthetic polymer.

Separately, a solution of ovomucoid dissolved in sodium hydrogencarbonate buffer solution of pH 6.8 is prepared, and this is added to the above suspension to obtain a polymer filler to which ovomucoid is bonded.

This filler and glutaraldehyde are added to phosphate buffer solution of pH 6.8 followed by stirring at 30° C. for 15 hours to form a glutarized ovomucoid (non-reduced type). Otherwise, further using sodium borohydride, stirring is carried out in phosphate buffer solution of pH 6.3 at 4° C. for 12 hours for reduction to form an optical isomer separating agent in which a formed glutarized ovomucoid (reduced type) is bonded to the synthetic polymer through amide bond and the cross-linking agent.

The important point of this invention resides in the use of ovomucoid whose molecule is partly modified in the separation of optical isomers, and this invention is never limited by kinds of carriers, bonding method of ovomucoid or derivatives thereof with carries, and modification methods of ovomucoid.

The separating agent according to this invention is, as described above, characterized in that it comprises a stationary phase in which the molecular structure of ovomucoid fixed to a carrier is partly modified, or a stationary phase in which ovomucoid whose molecular structure is partly modified is bonded to the carrier. Thus, this stationary phase is contained as an essential component in the separating agent according to this invention, and also other components in the separating agent, for example, silica gel, glass, cellulose, carbon, and polymers may be optionally selected and added, which can be properly conducted to improve separating efficiency.

The optical isomers mentioned herein mean chiral compounds having asymmetric carbon atoms in the molecules, and their examples can be found in many pharmaceuticals, including ibuprofen, ketoprofen, proglumide, flubiprofen, chlorophenecine, pindolol, chlorpheniramine, chloroprenaline, clemastine, alprenolol, oxprenolol, ascorbic acid, propranolol, and the like. In these compounds, a plurality of optical isomers having an enantiomeric relation to each other are present, integrally forming racemic bodies. The separating agent according to this invention applies to these racemic bodies, and is particularly effective for the separation of the optical isomers constituting the racemic bodies from them.

The separating agent according to this invention is mainly used in liquid chromatography. It may be used according to general operations in liquid chromatography, in which, for example, the separating agent of this invention is packed and charged in a column, a racemic body related to an optical isomer is charged therein, then a movable phase such as phosphate buffer solution, ethanol aqueous solution, and isopropanol is allowed to pass, and the desired optical isomer is separated by the difference in retention time.

BRIEF DESCRIPTION OF THE DRAWING

FIG. 1 is a graph showing the result of Example 1.

EXAMPLES

This invention is further described in detail according to the following specific examples, which never limit this invention.

Example 1

To 0.06 M phosphate buffer solution (pH. 6.8), 0.1 g of glutaraldehyde and 2 g of ovomucoid were added followed by stirring at 30° C. for 15 hours to synthesize a glutarized ovomucoid. The unreacted glutaraldehyde was removed by Sephadex G25 column chromatography to isolate the glutarized ovomucoid (non-reduced type). Or, further using sodium borohydride, stirring is carried out in phosphate buffer solution of pH 6.8 at 4° C. for 12 hours for reduction followed by purification, whereby a glutarized ovomucoid (reduced type) can be obtained.

The degree of modification by this reaction was confirmed by the following experiment. A sample in 2 ml of a ninhydrine reagent specified in the Japanese Pharmacopoeia was added to a solution in which 0.1 g of the above non-reduced type glutarized ovomucoid was dissolved in 50 ml of water, and a sample in which 2 ml of the ninhydrine reagent is added to a solution of 0.1 g of ovomucoid dissolved in 50 ml of water were prepared, and these were compared for absorbance at 560 nm. The absorbance of the sample using the glutarized ovomucoid was 0.05, and the absorbance of the sample using ovomucoid was 2.15. The above result showed that the amino group on the ovomucoid molecule is modified by this reaction.

Then, 2 g of a column filler (for example, Asahi Pack NH2P) in which a polyamine (for example, pentaethyl hexamine) was introduced into a hydrophilic polymer gel and 2 g of N,N-disuccinimidyl carbonate were added to 100 ml of 0.1 M sodium hydrogencarbonate buffer solution (pH 6.8) followed by stirring for one night, and the resulting solution was taken out and passed through a glass filter and washed the resulting activated synthetic polymer gel with water. Then the resulting activated synthetic polymer gel was suspended in 0.1 M sodium hydrogencarbonate buffer solution (pH 6.8) to prepare a suspension of the activated synthetic polymer gel. Separately, a solution in which 2 g of the non-reduced type or reduced type glutarized ovomucoid was dissolved in 30 ml of 0.1 M sodium hydrogencarbonate buffer solution (pH 6.8) was prepared. These solutions were respectively added to the above suspension, and each mixture was stirred and purified to obtain a separating agent of this invention. The obtained separating agent was charged in a steel column to form an optical isomer separating column.

Example 2

To 100 ml of 0.1 M sodium hydrogencarbonate buffer solution (pH 6.8), 3 g of aminopropyl silica gel and 2 g of N,N-disuccinimidyl carbonate were added followed by stirring for one night, and the resulting solution was passed through a glass filter and washed the resulting activated aminopropyl silica gel with water. Then the resulting activated aminopropyl silica gel was suspended in 0.1 M sodium hydrogencarbonate buffer solution (pH 6.8) to prepare a suspension of the activated aminopropyl silica gel.

Separately, a solution in which 2 g of ovomucoid was dissolved in 30 ml of 0.1 M sodium hydrogencarbonate buffer solution (pH 6.8) was prepared, and this solution was added to the above suspension to obtain an ovomucoid bonded silica gel filler. To 30 ml of 0.06 M phosphate buffer solution (pH 6.8), 2 g of this filler and 0.1 g of glutaraldehyde were added, and stirring was carried out at 30° C. for 15 hours to obtain a separating agent of this invention (non-reduced type). Further, 0.2 g of sodium borohydride was added thereto, and the mixture was stirred and reduced at 4° C. for 12 hours to obtain a separating agent of this invention (reduced type). The obtained separating agent was charged in a steel column to form an optical isomer separating column.

Example 3

To 100 ml of 0.06 M phosphate buffer solution (pH 6.8), 3 g of aminopropyl silica gel and 0.1 g glutaraldehyde were added followed by stirring at 30° C. for 15 hours, and the resulting solution was taken out and passed through a glass filter and washed the resulting glutarized silica gel with water. A solution of 2 g of ovomucoid dissolved in 30 ml of 0.1 M sodium hydrogencarbonate buffer solution (pH 6.8) was reacted with the resulting glutarized silica gel to glutarize the ovomucoid, and a separating agent of this invention was obtained. The obtained separating agent was charged in a steel column to form an optical isomer separating column.

Example 4A

An avomucoid bonded silica gel filler was prepared by use of aminopropyl silica gel in the same manner as in Example 2. This filler was dried in a phosphorus pentoxide desiccator, and suspended into 0.06 M phosphate buffer solution (pH 8.0), and 0.5 ml of 2,3-epoxypropanol was added thereto followed by stirring at room temperature for 24 hours to obtain a separating agent of this invention. The obtained separating agent was charged in a steel column to form an optical isomer separating column.

Example 4B

Into 0.06 M phosphate buffer solution, 2 g of ovomucoid was suspended, and 0.5 ml of 2,3-epoxypropanol was added thereto followed by stirring at room temperature for 24 hours to obtain a diolated ovomucoid. Then, 3 g of aminopropyl silica gel and 2 g of N,N-disuccinimidyl carbonate were added to 100 ml of 0.1 M sodium hydrogencarbonate buffer solution (pH 6.8) followed by stirring for one night, and the resulting solution was taken out, passed through a glass filter and washed the resulting activated aminopropyl silica gel with water. Then the resulting activated aminopropyl silica gel was suspended in 0.1 M sodium hydrogencarbonate buffer solution (pH 6.8) to prepare a suspension of the activated aminopropyl silica gel. Separately, a solution in which 2 g of diolated ovomucoid was dissolved in 30 ml of 0.1 M sodium hydrogencarbonate buffer solution (pH 6.8) was prepared, and this solution was added to the above suspension to obtain a separating agent of this invention. The obtained separating agent was packed and charged in a steel column to form an optical isomer separating column.

The degree of modification by this reaction was confirmed by the following experiment. To 150 mg each of the above separating agents (diolated ovomucoid-bonded silica gel) and ovomucoid-bonded silica gel, 2 ml of a ninhydrine reagent specified in the Japanese Pharmacopoeia was added followed by at 100° C. for 5 minutes. These suspensions were subjected to centrifugal separation after cooling, and their absorbances of the supernatants, at 560 nm, were measured.

The absorbance of the ovomucoid-bonded silica gel was 0.30, and the absorbance of the separating agent obtained by this example was 0.07. The above result showed that the amino group on the ovomucoid molecule is modified by this reaction, and the number of free amino groups is reduced.

Example 5A

An ovomucoid-bonded silica gel filler was obtained by use of aminopropyl silica gel in the same manner as in Example 2. A solution in which 0.225 ml of acetic anhydride was dissolved in 1.8 g of this filler and 1 ml of dioxane was added to 50 ml of 0.1 M phosphate buffer solution (pH 8.5), and the mixture was stirred at 25° C. for 30 minutes followed by purification to obtain a separating agent of this invention. The obtained separating agent was packed and charged in a steel column to form an optical isomer separating column.

Example 5B

To 0.1 M borate buffer solution (pH 8.5), 2 g of ovomucoid was added together with a solution in which 0.225 ml of acetic anhydride was dissolved in 1 ml of dioxane to obtain an acetylated ovomucoid. Then, 3 g of aminopropyl silica gel and 2 g of N, N-disuccinimidyl carbonate were added to 100 ml of 0.1 M sodium hydrogencarbonate buffer solution (pH 6.8) followed by stirring for one night, and the resulting solution was taken out, passed through a glass filter and washed the resulting activated aminopropyl silica gel with water. Then the resulting activated aminopropyl silica gel was suspended in 0.1 M sodium hydrogen-carbonate buffer solution (pH 6.8) to prepare a suspension of the activated aminopropyl silica gel. Separately, a solution in which 2 g of acetylated ovomucoid was dissolved in 30 ml of 0.1 M sodium hydrogencarbonate buffer solution (pH 6.8) was prepared, and this solution was added to the above suspension to obtain a separating agent of this invention. The obtained separating agent was charged in a steel column to form an optical isomer separating column.

The degree of modification by this reaction was confirmed by the following experiment. To 150 mg each of the above separating agents (acetylated ovomucoid-bonded silica gel) and the ovomucoid-bonded silica gel, 2 ml of a ninhydrine reagent specified in the Japanese Pharmacopoeia was added followed by heating at 100° C. for 5 minutes. These suspensions were subjected to centrifugal separation after cooling to obtain respective supernatants, and their absorbances at 560 nm were measured.

The absorbance of the ovomucoid-bonded silica gel was 0.30, and the absorbance of the separating agent obtained by this example was 0.01. The above result showed that the amino group on the ovomucoid molecule is modified by this reaction.

Resolution of the optical isomers from the racemic bodies using the optical isomer separating columns prepared in Examples 1 to 5 will be described.

Experimental Example 1

Using the optical isomer separating column prepared in Example 1 (reduced type), resolution in the enantiomers of benzoin was tried. As a mobile phase, 20 mM sodium dihydrogen phosphate containing 10% of ethanol was used at a flow rate of 0.8/min.

The result is shown in FIG. 1.

FIG. 1 shows that each optical isomer was separated by the separating agent of this invention.

Experimental Example 2

Using the column charged with the non-reduced type glutarized ovomucoid-bonded silica gel prepared in Example 2, and an optical isomer separating column as Comparative Example in which ovomucoid is bonded to silica gel, comparative experiments for resolving power to esters of propranolol were conducted.

Namely, enantiomers of propyl, butyl, and valeryl esters of propranolol were separated, and their respective chromatography parameters (distribution ratio, resolution coefficient) were determined.

The results are shown in Table 1.

TABLE 1

Comparison in Optical Resolving Power to Esters of Propranolol

| | $k_1'$ | α |
|---|---|---|
| Example 2 | | |
| Propyl ester | 0.65 | 1.12 |
| Butyl ester | 1.36 | 1.15 |
| Valeryl ester | 2.62 | 2.35 |
| Comparative Example | | |
| Propyl ester | 0.46 | 1.00 |
| Butyl ester | 1.03 | 1.18 |
| Valeryl ester | 1.99 | 2.04 |

In the table, $k_1'$ (k' of the enantiomer eluted earlier), $k_2'$ (k' of the enantiomer eluted later), and α were determined in accordance with following schemes.

Capacity factor $(k')=(t_i-t_o)/t_o$

Resolution coefficient $(\alpha)=k_2'/k_1'$

In the schemes, $t_i$ and $t_o$ represent retention times of a solute held by the column (i) and a solute never held by the column, respectively.

Table 1 showed that the separating agent of this invention has an optical resolving power more excellent than that of Comparative Example to esters of propranolol.

Experimental Example 3

Using the optical isomer separating column prepared in Example 4A and the optical isomer separating column as Comparative Example (See Exp. Example 2), comparative experiments for resolving power to propranolol were carried out.

The enantiomers of propranolol were separated by use of both the columns, and their respective chromatographic parameters (distribution ratio and resolution coefficient) were determined.

The results are shown in Table 2.

TABLE 2

Comparison in Optical Resolving Power to Propranolol

| | $k_1'$ | α |
|---|---|---|
| Example 4A | | |
| Propranolol | 0.99 | 1.47 |
| Comparative Example | | |
| Propranolol | 8.42 | 1.19 |

Table 2 showed that the separating agent of this invention has an optical resolving power more excellent than that of Comparative Example.

Experimental Example 4

The optical isomer separating column prepared in Example 4A was used to separate the enantiomers of alprenolol, and their chromatographic parameters (distribution ratio and resolution coefficient) were determined.

TABLE 3

Optical Resolving Power to Alprenolol

|  | $k_1'$ | α | Mobile phase |
|---|---|---|---|
| Alprenolol | 13.3 | 1.14 | 1 |
|  | 3.54 | 1.12 | 2 |
|  | 15.8 | 1.15 | 3 |
|  | 9.48 | 1.12 | 4 |
|  | 8.23 | 1.12 | 5 |
|  | 5.12 | 1.14 | 6 |

Mobile phase 1: 20 mM $NaH_2PO_4$+20 mM $Na_2HPO_4$ (96:4)/2-Propanol=99:1
Mobile phase 2: 20 mM $NaH_2PO_4$+20 mM $Na_2HPO_4$ (90:10)/2-Propanol=95:5
Mobile phase 3: 20 mM $NaH_2PO_4$+20 mM $Na_2HPO_4$ (50:50)/2-Propanol=95:5
Mobile phase 4: 20 mM $NaH_2PO_4$+20 mM $Na_2HPO_4$ (50:50)/2-Propanol=92.7:7.5
Mobile phase 5: 20 mM $NaH_2PO_4$+20 mM $Na_2HPO_4$ (96:4)/Ethanol=96:4
Mobile phase 6: 20 mM $NaH_2PO_4$+20 mM $Na_2HPO_4$ (96:4)/Ethanol=97.5:2.5

Table 3 showed that the separating agent according to this invention has an effective optical resolving power to alprenolol.

We claim:

1. A method of resolving a mixture of optical isomers comprising a step of contacting said mixture with an optical isomer separating agent comprising a stationary phase in which the molecular structure of ovomucoid bonded to a carrier is partially modified or a stationary phase in which ovomucoid having a partially modified molecular structure is bonded to a carrier, said partial modification of the ovomucoid molecular structure being achieved by glutarization, diolation or acylation thereof.

2. The method of claim 1, wherein the contacting of said mixture with said optical isomer separating agent is in a chromatographic column.

3. The method of claim 1, wherein the contacting of said mixture with said optical isomer separating agent is in a liquid chromatographic column.

4. The method of claim 1, wherein the partial modification of the ovomucoid molecular structure is achieved by glutarization thereof.

5. The method of claim 1, wherein the partial modification of the ovomucoid molecular structure is achieved by diolation thereof.

6. The method of claim 1, wherein the partial modification of the ovomucoid molecular structure is achieved by acylation thereof.

7. The method of claim 1, wherein said carrier is selected from the group consisting of silica gel, glass, cellulose, carbon and a synthetic polymer.

* * * * *